US012685582B2

(12) United States Patent
Pavignano et al.

(10) Patent No.: US 12,685,582 B2
(45) Date of Patent: Jul. 21, 2026

(54) ELECTROSURGICAL APPARATUS FOR THE TREATMENT, EVEN WITHOUT CONTACT, OF INNER AND/OR OUTER TISSUES

(71) Applicant: OTECH INDUSTRY S.R.L., Alessandria (IT)

(72) Inventors: Franco Pavignano, Alessandria (IT); Marco Arru, Alessandria (IT); Loris Ghione, Alessandria (IT)

(73) Assignee: OTECH INDUSTRY S.R.L., Alessandria (IT)

( * ) Notice: Subject to any disclaimer, the term of this patent is extended or adjusted under 35 U.S.C. 154(b) by 338 days.

(21) Appl. No.: 18/260,642

(22) PCT Filed: Jan. 11, 2022

(86) PCT No.: PCT/IB2022/050183
§ 371 (c)(1),
(2) Date: Jul. 7, 2023

(87) PCT Pub. No.: WO2022/149116
PCT Pub. Date: Jul. 14, 2022

(65) Prior Publication Data
US 2024/0307107 A1 Sep. 19, 2024

(30) Foreign Application Priority Data
Jan. 11, 2021 (IT) ........................ 102021000000335

(51) Int. Cl.
*A61B 18/00* (2006.01)
*A61B 18/12* (2006.01)
(Continued)

(52) U.S. Cl.
CPC ........ *A61B 18/148* (2013.01); *A61B 18/1206* (2013.01); *A61B 2017/00154* (2013.01);
(Continued)

(58) Field of Classification Search
CPC ... A61B 18/12; A61B 18/1206; A61B 18/148; A61B 2018/122; A61B 2018/1213
See application file for complete search history.

(56) References Cited

U.S. PATENT DOCUMENTS

| | | | |
|---|---|---|---|
| 4,200,104 A | 4/1980 | Harris | |
| 5,267,997 A | 12/1993 | Farin et al. | |

(Continued)

FOREIGN PATENT DOCUMENTS

| | | |
|---|---|---|
| WO | 2015118083 A1 | 8/2015 |
| WO | 2017013624 A1 | 1/2017 |

OTHER PUBLICATIONS

International Search Report and Written Opinion for Corresponding International Application No. PCT/IB2022/050183, 10 pages, May 27, 2022.

*Primary Examiner* — Daniel W Fowler
(74) *Attorney, Agent, or Firm* — LUCAS & MERCANTI, LLP

(57) ABSTRACT

An electrosurgical apparatus for the treatment, even without contact, of an inner and/or outer tissue is described. The apparatus includes a graspable handpiece and has an end fitted with a single active electrode, a generator system configured to generate a radio frequency electrical signal adapted to bias the active electrode to generate a plasma glow discharge between the active electrode and the tissue when the active electrode is in the proximity of the tissue. The apparatus also includes a stabilizing cable configured to close a circuit with the handpiece and the plasma glow discharge and to allow a return of a part of the current generated in the plasma discharge from the tissue toward the generator system.

13 Claims, 4 Drawing Sheets

(51) Int. Cl.
    *A61B 18/14*       (2006.01)
    *A61B 17/00*       (2006.01)

(52) U.S. Cl.
    CPC ............... *A61B 2017/00973* (2013.01); *A61B 2018/00577* (2013.01); *A61B 2018/00601* (2013.01); *A61B 2018/00702* (2013.01); *A61B 2018/0072* (2013.01); *A61B 2018/00726* (2013.01); *A61B 2018/00732* (2013.01); *A61B 2018/00767* (2013.01)

(56)               References Cited

U.S. PATENT DOCUMENTS

| | | | |
|---|---|---|---|
| 6,565,558 B1 | 5/2003 | Lindenmeier et al. | |
| 2008/0045941 A1 | 2/2008 | Fugo | |
| 2008/0071260 A1* | 3/2008 | Shores ............... | A61B 18/1206 606/34 |
| 2008/0108985 A1* | 5/2008 | Konesky ............. | A61B 18/042 606/27 |
| 2010/0145253 A1* | 6/2010 | Gutsol ..................... | A61N 1/40 606/49 |
| 2011/0301578 A1* | 12/2011 | Muniz-Medina ...... | A61B 90/92 606/1 |
| 2012/0245580 A1* | 9/2012 | Germain ............. | A61B 18/042 606/41 |
| 2016/0051313 A1* | 2/2016 | Canady ................ | A61B 18/042 606/39 |
| 2018/0169427 A1* | 6/2018 | Jeon ..................... | H05H 1/2406 |
| 2019/0104605 A1* | 4/2019 | Van Abeelen ....... | A61B 18/042 |

* cited by examiner

ELECTROSURGICAL APPARATUS FOR THE TREATMENT, EVEN WITHOUT CONTACT, OF INNER AND/OR OUTER TISSUES

CROSS-REFERENCE TO RELATED APPLICATIONS

This application is a 371 of PCT/IB2022/050183, filed Jan. 11, 2022, which claims the benefit of Italian Patent Application No. 102021000000335, filed Jan. 11, 2021.

FIELD OF THE INVENTION

The present invention refers to an apparatus for electrosurgery, in particular for carrying out a tissue cut or incision, or dissection, or for carrying out tissue ablation, or for a surface action that does not involve the removal of a tissue part on the body of a human or animal living being, or for carrying out a treatment with haemostatic effect on small bleeding areas and small vessels, in which such operations can take place even without contact.

BACKGROUND OF THE INVENTION

In the surgical and aesthetic sectors, the use of electrical apparatuses, which comprise a system for generating a radio frequency electrical signal and a handpiece adapted to be grasped by an operator and that comprises an end provided with an active electrode, which is electrically connected to the generator system, is known.

In particular, electrosurgery apparatuses are known in the sector which are adapted, by generating a plasma discharge, to an operation of tissue cut or incision, which are operated along a direction substantially perpendicular to the tissue, or tissue ablation, which occurs at the surface of the tissue, in a contactless mode, and removes part of the tissue.

The operating technology of said apparatuses is based on the phenomenon of ionisation of the surrounding atmospheric gas, in this case the air, by means of a generator that produces high-voltage pulses capable of causing the dielectric breakdown of the air, which turns from an insulating gas into a conductive gas. The resulting plasma is visible in the form of a strong glow.

In other words, the initially neutral (dielectric) gas is ionised by passing therein a strong high-voltage electromagnetic field which causes its dielectric breakdown, thereby ionising the gas and making it electrically conductive.

Thanks to the production of a plasma discharge, the tissue, in the proximity of the tip of the handpiece, is vaporised without causing the cells to explode, as is the case with the use of other electro-medical devices.

The plasma discharge is generated by moving the active electrode closer to the tissue, after which the electrode can be used. After the plasma is activated, if the active electrode comes into contact with the tissue, it causes a cut.

As regards apparatuses for electrosurgery, in general, including electrosurgical scalpels, it is necessary to use a return electrode or return plate which causes the electric circuit to be closed by means of the body of the living being, in order for the device to function. The consequences of using the aforesaid apparatuses are the significant flow of electric charges and currents and often scalds or burns on the body, on the area where the return electrode or return plate is applied.

Apparatuses which do not use a return plate are also known, and in order to carry out a cut of an epithelial tissue, they use an electrical signal applied to the cutting electrode with the following electrical characteristics: a high radio frequency signal between 40 kHz and 90 kHz, with an average power between 0.5 W and 20 W.

The electrical signal generated by the generator system is configured to generate a tissue cut or incision when the active electrode comes into contact with the tissue to be treated. The cut or incision is carried out by thermal effect.

In this type of apparatus, the electrical signal is configured in such a way that the emitted energy is transferred from the active electrode to the tissue through capacitive coupling. In particular, the cut is carried out by taking advantage of the difference in potential existing between the active electrode and the tissue and making a transfer of energy such as to vaporise the epithelial cells, which come into contact with the active electrode, by thermal effect.

While carrying out the cut, the electric circuit resulting from the active electrode is grounded by capacitive effect and there is a capacitive coupling both between the active electrode and the body of the living being, and between the same body and the earth, and the apparatus is free from using a return plate or dissipative plate.

However, these apparatuses have the disadvantage that part of the energy transferred from the active electrode to the tissue through capacitive coupling remains as surface energy at said tissue, causing negative effects, such as the generation of electric charges and currents which tend to flow through the human body.

An object of the present invention is to implement an electrosurgical apparatus capable of solving the drawbacks of the prior art.

Specifically, it is an object of the present invention to avoid the typical consequences of the use of electrosurgical apparatus, in particular the passage through, or the deposition on, the tissue of significant amounts of electric charges and currents, such as to sometimes cause spasms, scalds or burns on the body of the living being in the area where the return electrode or return plate is applied.

A further object of the present invention is to provide an electrosurgery apparatus of an improved and reliable type, and which at the same time can be manufactured simply and economically.

SUMMARY OF THE INVENTION

These and other objects are achieved by means of an apparatus for electrosurgery as described herein.

In particular, the invention is directed to an electrosurgical apparatus for carrying out, even without contact, a tissue cut or incision, or a tissue dissection, or a tissue ablation, or a treatment with haemostatic effect on small bleeding areas and small vessels on the body of a human or animal living being;

a surface treatment on the outer tissues, with surgical or aesthetic purposes, on the body of a living being.

The following terminology is used in the following description.

tissue cut or incision: a separation operation which involves an action along a direction substantially perpendicular to the tissue;

dissection: a separation operation which involves an action along a direction longitudinal to the fibres of the tissue, in order to separate the different layers thereof;

tissue ablation: operation that takes place at the surface of the tissue, in a contactless mode, to remove part of tissue;

surface action: less invasive operation than the tissue ablation, which does not involve the removal of a part of tissue.

According to an aspect, this electrosurgical apparatus comprises:

at least one handpiece adapted to be grasped by an operator and comprising an end fitted with an active electrode;

a generator system operatively and electrically connected to said handpiece, configured to generate a radio frequency electrical signal adapted to bias said active electrode so as to generate a plasma glow discharge between said active electrode and said tissue when said active electrode is in the proximity of said tissue.

Advantageously, by means of this electrosurgical apparatus, it is possible to carry out several operations on the inner and/or outer tissue.

According to an aspect of the present invention, the electrosurgical apparatus comprises a stabilising cable. Said stabilising cable is configured to create a circuit with the at least one handpiece and said plasma glow discharge. The stabilising cable is further configured to allow the recovery of a residual surface energy, which is not grounded by means of the capacitive coupling alone between the body of the living being and the surrounding environment, from said tissue. In particular, the recovery from said tissue of a residual surface energy is configured as a current return from the tissue toward the generator system.

Advantageously, such a stabilising cable allows the return toward the machine of at least part of the current generated by the plasma discharge and present on the tissue in the form of surface energy, which would not otherwise be dispersed by capacitive effect between the tissue and the surrounding environment.

In other words, the presence of such a stabilising cable allows the closure of a circuit with said handpiece, to allow the recovery of possible residual surface energy which is not grounded by means of the capacitive coupling alone on the body of a living being with the surrounding environment, through the return of the current from said tissue.

Thereby, advantageously, there is a return of the current toward the machine and accumulations of surface energy on the tissue are avoided, with potentially negative effects and, in particular, the generation of excessive unwanted muscle tremors or spasms. According to an aspect, the electrosurgical apparatus, according to the invention comprises a plurality of handpieces operatively and electrically connected to such generator system and which can be alternatively powered by said generator system. Advantageously, according to this aspect, it is possible to carry out surgical operations of various nature, such as cut, dissection, ablation or haemostasis, superficial, surgical or aesthetic treatments, with the same machine, by using several dedicated handpieces.

This aspect makes the described electrosurgical apparatus very versatile and also involves a cost saving since different apparatus is not necessary to carry out different functions. According to an aspect of the electrosurgical apparatus according to the invention, such radio frequency electrical signal is adapted to bias the active electrode so as to generate a plasma glow discharge between this active electrode and the tissue mass when the active electrode is at a distance between 0.5 mm and 3 mm from the tissue mass.

According to a further aspect of the electrosurgical apparatus according to the invention, the generator system comprises:

a logical control unit configured to receive signals, process such signals and send further drive signals;

a power supply circuit operatively connected to such logical control unit and such at least one handpiece, which is configured to electrically power the at least one handpiece through such radio frequency electrical signal.

In particular, according to this aspect, the logical control unit is configured to drive the power supply circuit by regulating at least one of its operating parameters selected from:

power of the radio frequency electrical signal, up to a maximum value of 20 W;

frequency of the radio frequency electrical signal, up to a maximum value of 100 kHz;

output current up to a maximum value of 0.1 A;

peak-to-peak value of the output voltage, up to a maximum of 5.0 kV;

duty cycle in a value between 10% and 80%.

In particular, according to this aspect, the logical control unit is configured to drive such power supply circuit by regulating at least one of its operating parameters in a pre-set configuration selected from:

cut and dissection: wherein the peak-to-peak value of the output voltage is less than 1.3 kV and wherein the active electrode operates by contact to produce a cut or dissection on the tissue (T);

ablation and surface treatments: wherein the peak-to-peak value of the output voltage is between 1.3 kV and 2.2 kV and wherein the active electrode operates without contact to produce ablation or a surface treatment on the tissue (T);

haemostasis: the peak-to-peak value of the output voltage is between 2.2 kV and 5.0 kV and wherein the active electrode operates without contact to produce a haemostasis at the tissue (T).

Advantageously, also in the cut and dissection configurations and in the ablation and surface treatment configurations, the electrosurgical apparatus also carries out simultaneously a secondary haemostatic action. Specifically, therefore, in these configurations, the haemostatic action is carried out simultaneously with the primary actions of cut, dissection, ablation or surface treatment.

Advantageously, according to this aspect, by means of the electrosurgical apparatus according to the invention, it is possible to achieve effective results, in particular:

during the actions carried out with cut and dissection by means of a signal lower than 1.3 kV in which the active electrode operates by contact;

during the actions carried out with ablation and surface treatments in which the peak-to-peak value of the output voltage is between 1.3 kV and 2.2 kV and in which the active electrode operates without contact;

during the haemostasis carried out as simultaneous action with the other techniques, by means of the signals and values of the respective techniques;

during specific actions of haemostasis, in which the peak-to-peak value of the output voltage is between 2.2 kV and 5.0 kV.

According to a further aspect of the electrosurgical apparatus according to the present invention, when the power supply circuit is in the haemostasis configuration, it is configured to generate a radio frequency electrical signal having a form of pulsed signal. Advantageously, according to this aspect, it is possible to achieve an effective haemostasis since it is possible to generate a pulsed signal, such as to concentrate the power supplied in a short pulse and to achieve a higher output voltage.

According to a further aspect, the electrosurgical apparatus according to the invention comprises a user interface operatively connected to the logical control unit, which comprises, in turn, first regulating means arranged on a casing of the generator system, which can be actuated by an operator and are configured to regulate the at least one operating parameter of the power supply circuit.

Furthermore, according to a further aspect, the user interface can comprise second regulating means positioned on the handpiece, which can be actuated by an operator and are configured to regulate at least one operating parameter of the power supply circuit and/or to actuate the electrosurgical apparatus.

Advantageously, according to this aspect, an operator can regulate one or more operating parameters during the electrosurgery operation, without having to move away from the location where the tissue treatment takes place.

According to a further aspect, the surgical apparatus according to the invention comprises an actuating device, preferably a pedal, operatively connected to the logical control unit and configured to drive the power supply circuit.

BRIEF DESCRIPTION OF THE FIGURES

Further characteristics and advantages of the present invention will become clearer in the following description, which was made by way of example with reference to the accompanying figures, in which.

DETAILED DESCRIPTION OF SOME EMBODIMENTS OF THE PRESENT INVENTION

Figure 1A:
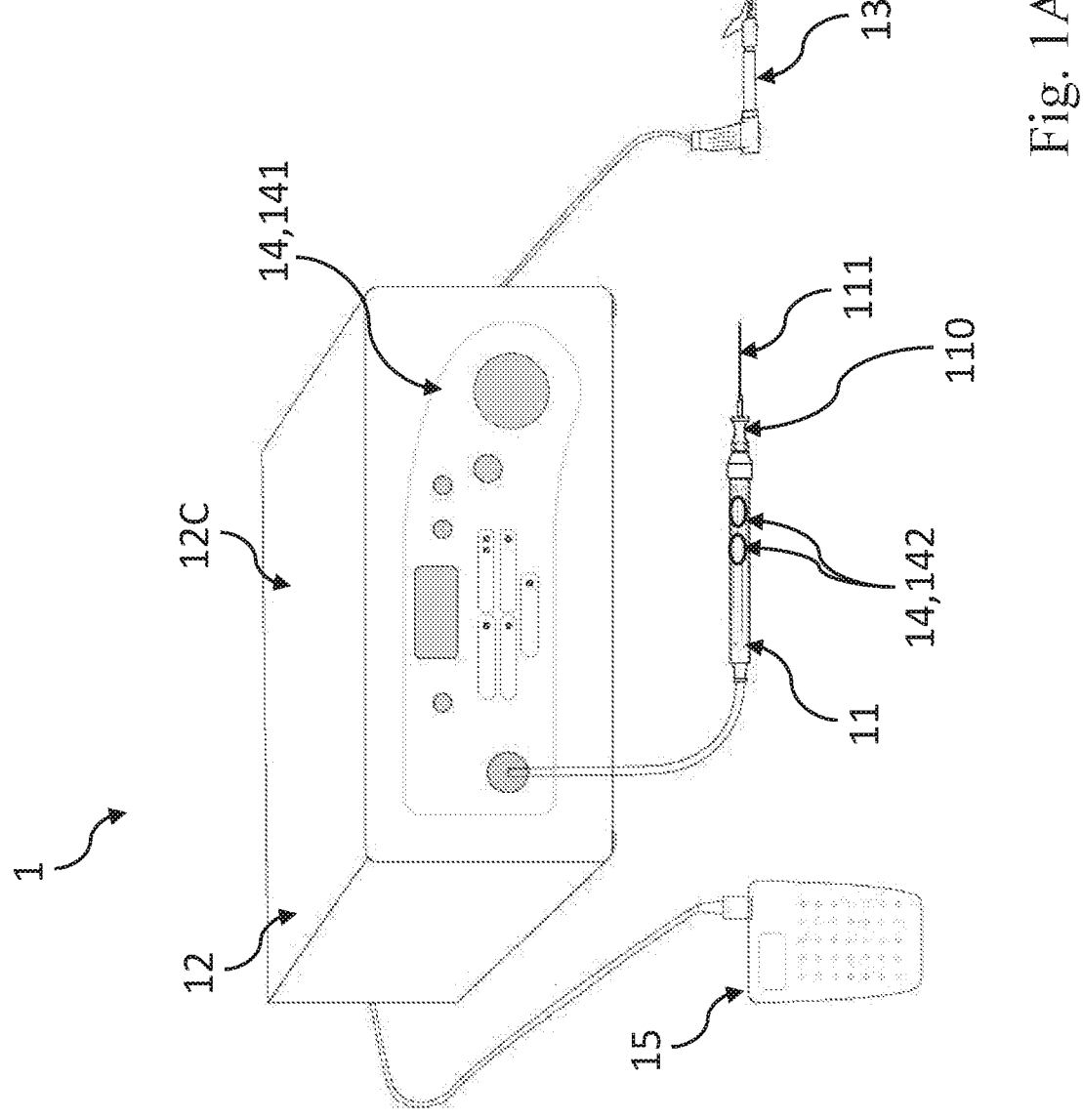
FIG. 1A depicts, according to a perspective view, the electrosurgical apparatus in an embodiment.

FIG. 1A depicts an embodiment of the electrosurgical apparatus for the treatment, even without contact, of the inner and/or outer tissues of a human or animal living being, hereinafter referred to simply as electrosurgical apparatus 1 or simply apparatus 1. Said electrosurgical apparatus 1 is configured, according to modes which will be clearer later in the present detailed description, for carrying out even without contact:

on the body of a human or animal living being, a tissue cut or incision, or a tissue dissection, or a tissue ablation, or a treatment with haemostatic effect on small bleeding areas and small vessels, a surface treatment on the outer tissues, with surgical or aesthetic purposes, on the body of a living being.

According to what is depicted in the attached figures, the electrosurgical apparatus 1 comprises at least one handpiece 11, 11' adapted to be grasped by an operator O, generally a surgeon, adapted to carry out a treatment on said inner and/or outer tissue T of the living being P.

Said at least one handpiece 11, 11' comprises an end 110 fitted with an active electrode 111.

Figure 2:
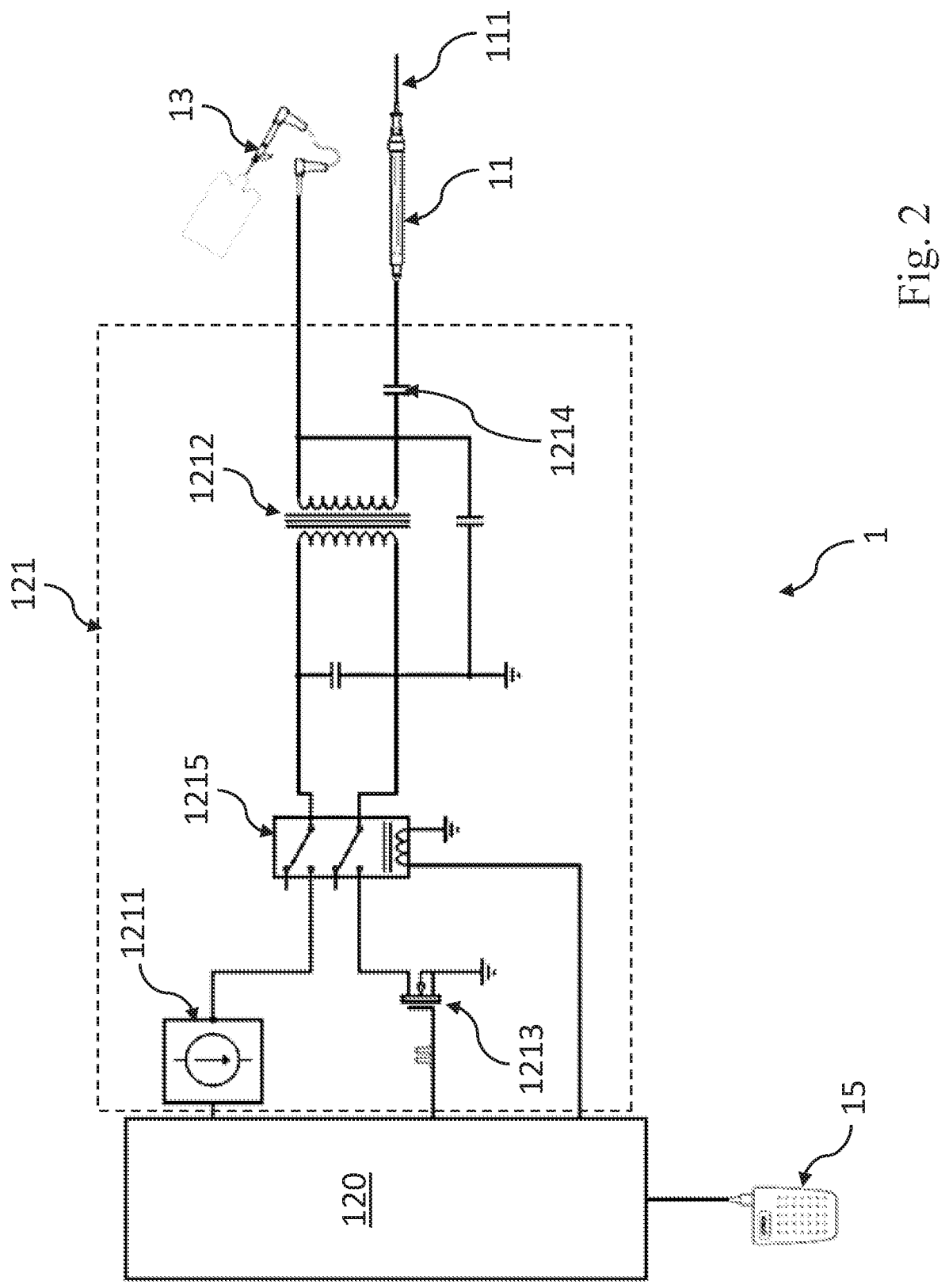
FIG. 2 depicts, according to a partially simplified block circuit view, further elements of the electrosurgical apparatus referred to in FIG. 1A.
Figure 3:
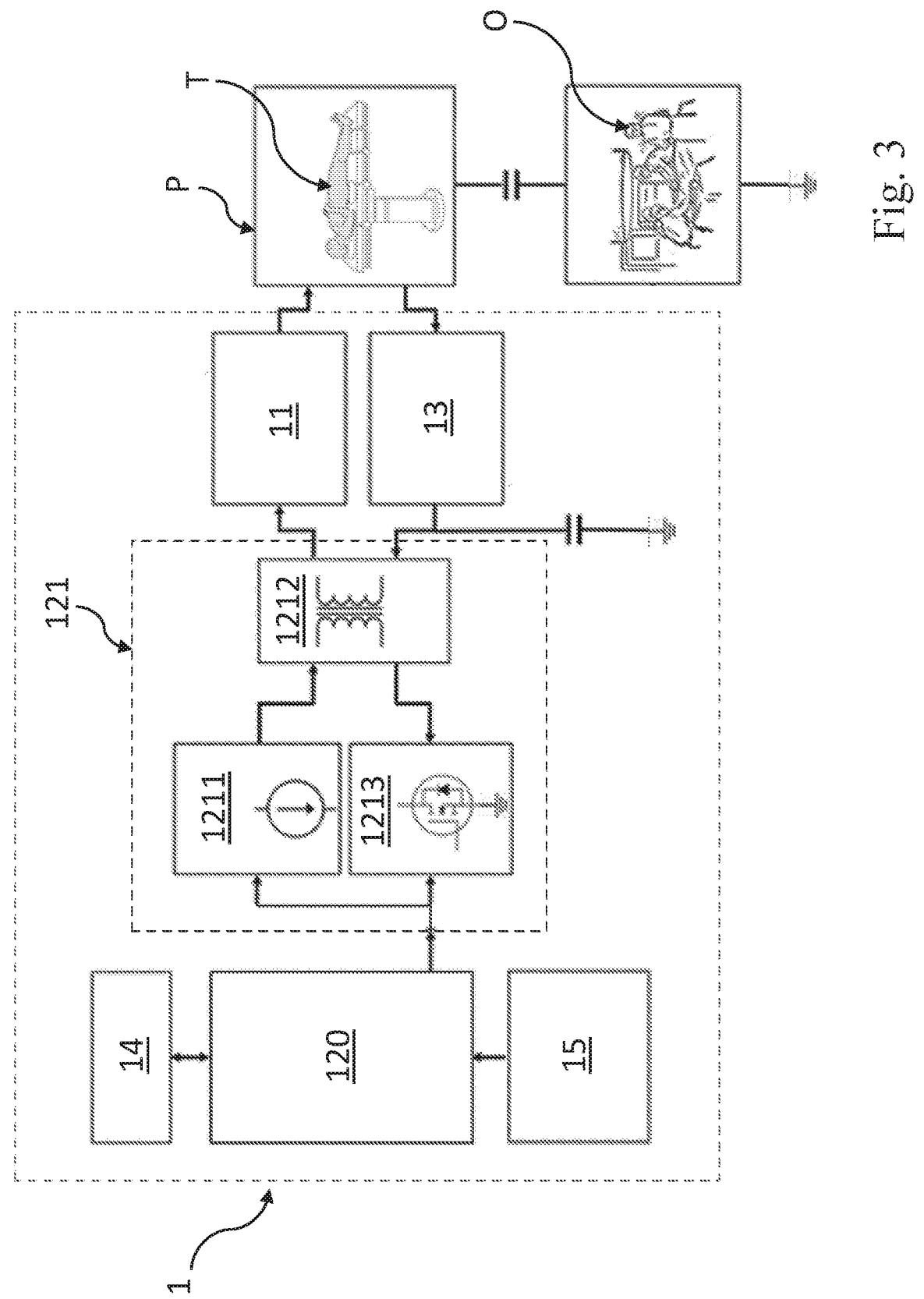
FIG. 3 depicts, according to a further block diagram, the electrosurgical apparatus referred to in FIG. 1A.

According to the embodiment depicted in FIGS. 1A, 2 and 3, the electrosurgical apparatus 1 comprises a single handpiece 11 possibly interchangeable with a different handpiece having different characteristics.

According to other embodiments, the electrosurgical apparatus 1 comprises a plurality of handpieces 11, 11' selectively operable according to modes which will be clearer hereinafter. In the embodiment depicted in FIG. 1B, the electrosurgical apparatus 1 comprises two selectively operable handpieces 11, 11'.

Advantageously, by having at least two selectively operable handpieces 11, 11', it is possible to carry out different treatments, preferably one for each handpiece, by selecting the most suitable handpiece, without having to replace the handpiece, as will be clearer hereinafter.

According to another aspect, the electrosurgical apparatus 1 comprises a generator system 12. Said generator system 12 is operatively and electrically connected to said handpiece 11 or several handpieces 11, 11', if the embodiment provides more than one handpiece. According to the embodiment depicted, the at least one handpiece 11, 11' is connected to the generator system 12 by means of a wired connection.

Figure 1B:
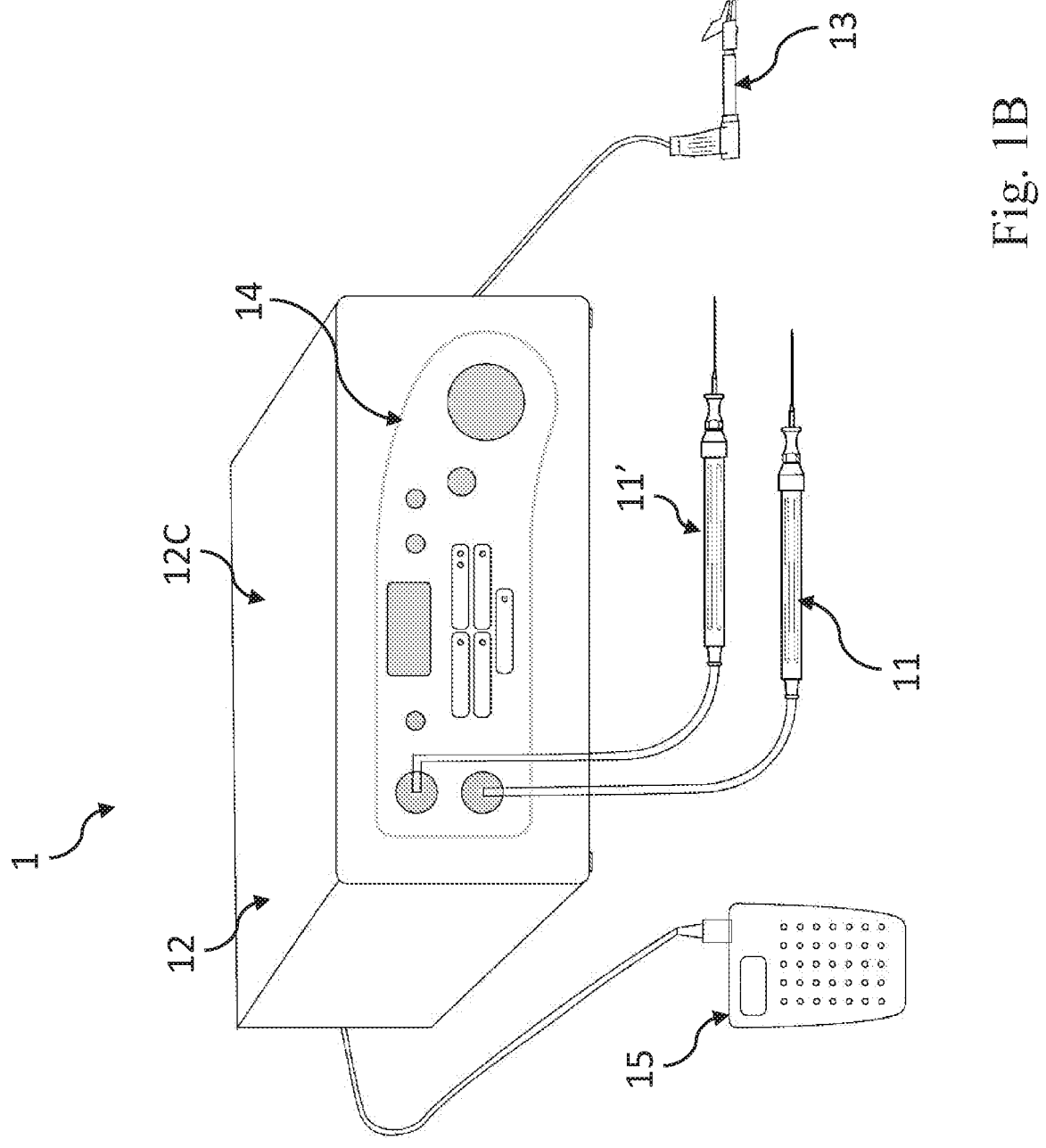
FIG. 1B depicts, according to a perspective view, the electrosurgical apparatus in a further embodiment.

In the embodiment of FIGS. 1A and 1B, the generator system 12 comprises a casing 12C configured to contain and protect further components of the same generator system 12.

The generator system 12 is configured to generate a radio frequency electrical signal adapted to bias said active electrode 111 so as to generate a plasma glow discharge between said active electrode 111 and said tissue T when said active electrode 111 is in the proximity of said tissue T.

In particular, said radio frequency electrical signal is adapted to bias said active electrode 111 so as to generate a plasma glow discharge between said active electrode 111 and said tissue T when said active electrode 111 is in the proximity of said tissue T, in particular at a distance of between 0.5 mm and 3 mm.

Depending on the operation to be carried out, the handpiece 11, 11' can be used in contact with the tissue T of the living being P, e.g. to carry out a cut or dissection, or without contact, as in the case of an ablation or surface treatments or a haemostatic action of said tissue T. As will be clearer below, different operations correspond to different characteristics of the radio frequency electrical signal generated by the generator system 12 which powers the active electrode 111.

According to what is depicted in FIG. 2 or 3, the generator system 12 comprises a logical control unit 120 configured to receive signals, process said signals and send further drive signals. Specifically, the logical control unit 120 is configured to regulate the process of generating the radio frequency electrical signal.

Preferably, said logical control unit 120 comprises at least one microprocessor adapted to communicate with the electronic components of the generator system 12. Still preferably, the logical control unit 120 comprises a plurality of microprocessors, each designated to carry out specific functions.

Still according to what is depicted in FIG. 2 or 3, the generator system 12 comprises a power supply circuit 121. Said power supply circuit 121 is operatively connected to said logical control unit 120 and said at least one handpiece 11, 11'.

In particular, the power supply circuit 121 is configured to electrically power the at least one handpiece 11, 11' by means of said radio frequency electrical signal, i.e. it is configured to generate said radio frequency electrical signal and transmit it to the at least one handpiece 11, 11'.

According to an aspect, the control unit 120 is configured to drive the power supply circuit 121 in the process of generating the radio frequency electrical signal.

Specifically, the logical control unit 120 is configured to drive said power supply circuit 121 by regulating at least one of its operating parameters selected from:

power of the radio frequency electrical signal, up to a maximum value of 20 W;

frequency of the radio frequency electrical signal, up to a maximum value of 100 kHz;

output current up to a maximum value of 0.1 A;

peak-to-peak value of the output voltage, up to a maximum of 5.0 kV;

duty cycle in a value between 10% and 80%.

Preferably, the logical control unit 120 is configured to drive said power supply circuit 121 by regulating at least one of its operating parameters in a pre-set configuration selected from:

cut and dissection: wherein the peak-to-peak value of the output voltage is less than 1.3 kV and wherein the active electrode operates by contact in order to produce a cut or dissection on the tissue T;

ablation and surface treatments: wherein the peak-to-peak value of the output voltage is between 1.3 kV and 2.2 kV and wherein the active electrode works without contact to produce ablation or a surface treatment on the tissue T;

haemostasis: the peak-to-peak value of the output voltage is between 2.2 kV and 5.0 kV and wherein the active electrode works without contact to produce a haemostasis at the tissue T.

It should be noted that, also in the cut and dissection configurations and in the ablation and surface treatment configurations, the electrosurgical apparatus 1 can simultaneously also carry out a secondary haemostatic action. Specifically, therefore, in these configurations, the haemostatic action is carried out simultaneously with the primary actions of cut, dissection, ablation or surface treatment.

Advantageously, this way, it is possible to vary the operating parameters of the power supply circuit 121 according to the type of surgical operation to be carried out.

Other operating parameters affect the efficiency of the operation to be carried out by the handpiece. By way of example, by varying the frequency or operating cycle, it is possible to increase the efficiency of the operation carried out (e.g. a deeper cut or ablation action) which will be carried out by means of the handpiece 11, 11'.

In short, depending on the characteristics of the tissue T to be treated, it is possible to vary the combination of operating parameters of the power supply circuit 121 in order to perform an optimal treatment of said tissue T.

According to an aspect of the present description, the power supply circuit 121, when is in the haemostasis configuration carried out as a specific action, is configured to generate said radio frequency electrical signal having a pulsed signal form. Thanks to the characteristics of a pulsed signal, it is possible to concentrate the power supplied in a short pulse and to achieve an output voltage higher than the radio frequency electrical signal used in the cut or dissection or ablation or surface action configurations, thus allowing the quick blood clotting.

According to an embodiment, the generator system 12, and in particular the power supply circuit 121, is powered by means of an external electric current source, such as the 220/110 V and 50/60 Hz power distribution network, through a switchable power supply unit not depicted.

According to another embodiment, the generator system 12, and in particular the power supply circuit 121, is powered by means of an internal electric current source, such as e.g. a battery.

As depicted in FIGS. 1A and 1B, the electrosurgical apparatus 1 comprises a stabilising cable 13 operatively and electrically connected to said generator system 12. Preferably, the stabilising cable 13 is connected to the generator system 12 by a wired connection. Said stabilising cable 13 is configured to create a circuit with said handpiece 11, 11' and said plasma glow discharge, to allow the recovery of the residual surface energy which is not grounded by means of the capacitive coupling alone of the body of the living being with the surrounding environment.

The stabilising cable 13 is in fact configured to recover this fraction of surface energy not grounded, through the return of the current from the treated tissue. On the contrary, most of the surface energy generated on the patient's body is grounded by capacitive effect 133 with the surrounding environment and the current then re-enters the circuit by means of a decoupling capacitor 132.

In particular, the recovery of surface energy is supported by the combination of two contributions: a return of current from the tissue T to the generator system 12 through the stabilising cable 13 and a return of the current grounded by the capacitive coupling 133 between the patient and the surrounding environment through the capacitor 132.

It should be noted that the term "capacitive coupling 133" and the respective reference numeral in FIG. 3 do not refer to a physical component of the circuit, but to a virtual capacitive coupling between the patient and the surrounding environment.

Thereby, advantageously, there is a return of current toward the generator system 12 and surface energy residues on the tissue are avoided, with potentially negative effects and, in particular, the generation of excessive unwanted muscle tremors or spasms.

According to an aspect, the stabilising cable 13 comprises, at one end thereof, a fastening element, preferably pliers, configured to stably connect, directly or indirectly, the same stabilising cable 13 to the tissue T.

According to another aspect of the present description, the electrosurgical apparatus 1 comprises a user interface 14. Specifically, the user interface 14 is connected to said logical control unit 120 to send and receive signals.

According to what is depicted in FIG. 1A, the user interface 14 comprises first regulating means 141, which can be actuated by an operator O. Said first regulating means 141 are arranged on the casing 12C of the generator system 12 so that they can be easily reached by the operator O. Specifically, said first regulating means 141 are configured to regulate said at least one operating parameter of the power supply circuit 121, subject to communication with the logical control unit 120 which always acts as a bridge between said user interface 14 and the power supply circuit 121.

Preferably, the first regulating means 141 comprise a plurality of commands operable by the operator O for setting at least one operating parameter of the power supply circuit 121.

Still preferably, the user interface 14 comprises acoustic and/or visual warning means adapted to detect and communicatively signal to the operator O the change of an operating parameter or any defect related to the operation of the oscillator and/or the inner temperature of the electrosurgical apparatus 1. In particular, the first regulating means 14 can comprise a sensitive screen, i.e. a touch screen, which also acts as a command for regulating at least one operating parameter of the power supply circuit 121.

According to what is depicted in FIG. 1A, the user interface 14 further comprises second regulating means 142 which can be actuated by an operator O and which are positioned on said at least one handpiece 11, 11'. Like the first regulating means 141, the second regulating means 142 are also configured to regulate at least one operating parameter of the power supply circuit 121.

According to a further aspect of the present description, the electrosurgical apparatus 1 comprises an actuating device 15 operatively connected to the logical control unit 120 and configured to drive said power supply circuit 121.

Preferably, as depicted in the attached figures, said actuating device 15 comprises at least one pedal which can be operated by said operator O by means of a foot pressure.

In the specific actuation, it is configured to close or open the power supply circuit 121 so as to allow the at least one handpiece 11, 11' to be powered by means of said radio frequency electrical signal.

In the embodiment depicted in FIG. 1B, the apparatus according to the invention comprises a plurality of handpieces 11, 11' and the actuating device 15 is configured to alternatively select the handpiece 11, 11' to be powered by the generator system 12. In this configuration, the power supply device 15 acts as a selector, by closing the power supply circuit 121 for the selected handpiece 11, 11' and opening all the power supply circuits 121 of the remaining handpieces 11, 11'.

An embodiment of the power supply circuit 121, depicted in FIG. 2, is now described in greater detail, which please remember it is configured to generate a radio frequency electrical signal to power the active electrode 111 of the handpiece 11, 11' with said radio frequency electrical signal, and to be driven by said logical control unit 120.

According to what is depicted, the power supply circuit 121 comprises a current generator 1211 configured to generate a current of drivable amplitude which affects the energy associated with the radio frequency electrical signal powering the active electrode 111. Said current generator 1211 is operatively connected to the logical control unit 120 to be driven by the latter so as to vary at least one operating parameter for generating the radio frequency electrical signal.

The power supply circuit 121 comprises at least one transformer 1212. Said at least one transformer 1212 is configured to carry out functions of voltage boosting, decoupling and frequency filtering of the radio frequency electrical signal. In the embodiment depicted in the attached figures, the power supply circuit comprises only one transformer 1212. However, alternative embodiments comprising multiple transformers 1212 are provided by the present invention. Advantageously, the presence of multiple transformers allows greater flexibility in the process of generating the radio frequency electrical signal for powering the active electrode 111 and, therefore, more ways of generating plasma that are useful to the operator.

For example, if two handpieces 11, 11' are provided in the electrosurgical apparatus 1, the power supply circuit 121 can comprise two independent transformers 1212 for powering each handpiece 11, 11' in the most appropriate manner.

According to what is depicted, the current generator 1211 is connected to a primary winding of the transformer 1212 or the transformers 1212, whereas the handpiece 11 and the stabilising cable 13 are connected to a secondary winding of the same transformer 1212 or the same transformers 1212.

The power supply circuit 121 further comprises a switch 1213. According to what is depicted, the switch 1213 is operatively connected to the primary winding of the transformer 1212. Preferably, said switch 1213 comprises a semiconductor element, even more preferably a transistor, such as e.g. a MOSFET. Said switch 1213 is operatively connected to the logical control unit 120 and is configured to determine the switching frequency of the power supply circuit 121.

The switch 1213 is configured to time the electrical signal coming from the current generator 1211, by supplying it to the transformer 1212. Then, the transformer 1212 increases the voltage and, by means of the hysteresis effect, causes the signal to become sinusoidal, which is then supplied to a capacitive decoupling stage 1214 so that the energy is transferred to the handpiece 11 and in particular to the active electrode 111.

According to the embodiment of FIG. 2, the power supply circuit 121 comprises a switch 1215 operatively connected to the actuating device 15, which is configured to selectively open or close the power supply circuit 121.

As an alternative to the above, it will be clear to a person skilled in the art that a different structure can be designed as regards said plurality of output components, provided that there is still the possibility of generating and transmitting a periodic (e.g. sinusoidal) signal to at least one final capacitive stage, so that the latter can supply an adapted electrical signal to the active electrode.

The operating steps carried out by the operator O while using the electrosurgical apparatus 1 during the treatment of tissue T, whether tissue cut or incision, dissection, ablation, surface treatments or haemostasis, will now be briefly described.

First, the operator O connects the stabilising cable 13 to the tissue T to be treated by the electrosurgical apparatus 1. Specifically, the stabilising cable 13 is stably connected to the tissue T by means of said fastening element depicted in the attached figures as pliers. Said connection can be direct, by means of the direct contact between the fastening element of the stabilising cable 13 and the tissue T, or indirect, by means of the contact between the fastening element and a conductor element, preferably disposable, previously placed in contact with the tissue T.

Subsequently, the operator O carries out the treatment of the tissue T by means of the handpiece 11 or by means of the handpieces 11, 11', which please remember they can be operated selectively in order to ensure flexibility of treatment. As described above, the at least one handpiece 11, 11' is powered by the generator system 12 in order to bias the active electrode 111 and generate the plasma glow discharge necessary for the treatment of the tissue T.

Please note that, during the treatment of the tissue T, the stabilising cable 13 remains stably connected to the aforesaid tissue T so as to allow recovery of a residual surface energy, which is not grounded by means of the capacitive coupling 133 alone between the living being P and the surrounding environment. Specifically, said recovery of residual surface energy takes the form of a current return from the tissue T toward the generator system 12, while the grounded surface energy re-enters the circuit by means of a decoupling capacitor 132. Thereby, advantageously, the possibility of the residual surface energy accumulating at the tissue T, possibly causing spasms at the same tissue, is excluded.

Once the treatment of the tissue T has been completed, the stabilising cable 13 is detached from the tissue T.

The invention claimed is:

1. An electrosurgical apparatus comprising:

a handpiece adapted to be grasped by an operator and comprising an end fitted with an active electrode;

a generator system operatively and electrically connected to said handpiece, configured to generate a radio frequency electrical signal adapted to bias said active electrode so as to generate a plasma glow discharge between said active electrode and said tissue when said active electrode is in the proximity of said tissue; and a stabilizing cable, operatively and electrically connected to said generator system, configured to create a circuit with said handpiece and said plasma glow discharge, to allow the recovery from said tissue of a residual surface energy, which has not been grounded through the capacitive coupling alone between a living being and the surrounding environment, through a current return from the tissue towards the generator system, wherein the recovery of the residual surface energy from the tissue is achieved by a combination of a first contribution and a second contribution, the first contribution including a return of current from said tissue towards the generator system through the stabilizing cable and the second contribution including a return of the current grounded by the capacitive coupling between the living being and the surrounding environment towards the generator system through a decoupling capacitor.

2. The electrosurgical apparatus according to claim 1 further comprising a plurality of handpieces operatively and electrically connected to said generator system, which can be alternately powered by said generator system.

3. The electrosurgical apparatus according to claim 1, wherein said radio frequency electrical signal is adapted to bias said active electrode so as to generate a plasma glow discharge between said active electrode and said tissue when said active electrode is at a distance between 0.5 mm and 3 mm from said tissue.

4. The electrosurgical apparatus according to claim 1, wherein the generator system comprises:

a logical control unit configured to receive signals, process said signals and send further drive signals; and a power supply circuit operatively connected to said logical control unit and said at least one handpiece, which is configured to electrically power the at least one handpiece through said radio frequency electrical signal.

5. The electrosurgical apparatus according to claim 4, wherein said logical control unit is configured to drive said power supply circuit by regulating at least one of its operating parameters selected from:

power of the radio frequency electrical signal, up to a maximum value of 20 W;

frequency of the radio frequency electrical signal, up to a maximum value of 100 kHz;

output current up to a maximum value of 0.1 A;

peak-to-peak value of the output voltage, up to a maximum of 5.0 kV; and duty cycle in a value between 10% and 80%.

6. The electrosurgical apparatus according to claim 5, wherein said logical control unit is configured to drive said power supply circuit by regulating at least one of its operating parameters in a pre-set configuration selected from:

cut and dissection: wherein the peak-to-peak value of the output voltage is less than 1.3 kV and wherein the active electrode operates by contact to produce a cut or dissection on the tissue;

ablation and surface treatments: wherein the peak-to-peak value of the output voltage is between 1.3 kV and 2.2 kV and wherein the active electrode operates without contact to produce ablation or a surface treatment on the tissue; and haemostasis: the peak-to-peak value of the output voltage is between 2.2 kV and 5.0 kV and wherein the active electrode operates without contact to produce a haemostasis at the tissue.

7. The electrosurgical apparatus according to claim 6, wherein the power supply circuit is configured to generate said radio frequency electrical signal having a pulsed signal form when it is in the haemostasis configuration.

8. The electrosurgical apparatus according to claim 5, further comprising a user interface operatively connected to said logical control unit, in turn comprising first control commands arranged on a casing of the generator system, which can be actuated by an operator and are configured to regulate said operating parameter of the power supply circuit.

9. The electrosurgical apparatus according to claim 8, wherein said user interface comprises second control commands positioned on said handpiece, which can be actuated by an operator and are configured to regulate an operating parameter of the power supply circuit and/or to actuate the electrosurgical apparatus.

10. The electrosurgical apparatus according to claim 4, further comprising an actuating device operatively connected to the logical control unit (120) and configured to drive said power supply circuit.

11. The electrosurgical apparatus of claim 10, wherein the actuating device is a pedal.

12. The electrosurgical apparatus of claim 1, wherein the decoupling capacitor is connected between ground and the generator system and is configured to conduct the current grounded by the capacitive coupling between the living being and the surrounding environment toward the generator system.

13. The electrosurgical apparatus of claim 1, wherein the stabilizing cable is connected to the generator system by a stabilizing cable connection and the decoupling capacitor is connected between ground and the stabilizing cable connection.

* * * * *